United States Patent [19]

Harrison

[11] 4,024,177

[45] May 17, 1977

[54] PHENYL ISOCYANATE DERIVATIVES OF RADIATION CURABLE OLIGOMERS

[76] Inventor: Stuart A. Harrison, 4432 Colfax Ave., Minneapolis, Minn. 55440

[22] Filed: Oct. 8, 1975

[21] Appl. No.: 620,674

[52] U.S. Cl. ................................ 260/472; 526/304
[51] Int. Cl.² ...................................... C07C 125/06
[58] Field of Search .................... 260/471 C, 472

[56] References Cited

UNITED STATES PATENTS

| | | | |
|---|---|---|---|
| 3,856,830 | 12/1974 | Kuehn | 260/471 C X |
| 3,859,332 | 1/1975 | Baker | 260/471 C |

*Primary Examiner*—Richard L. Raymond

[57] ABSTRACT

Phenyl isocyanate derivatives of oligomers, derived from polyhydroxy aliphatic hydrocarbons, formaldehyde and acrylamide, which cure upon exposure to radiation to films which retain electrical charges.

1 Claim, No Drawings

PHENYL ISOCYANATE DERIVATIVES OF RADIATION CURABLE OLIGOMERS

This invention relates to compositions of matter which can be cured by radiation to produce coatings or films which retain surface electrical charges. These coatings and films are particularly useful in dielectric printing. More especially, this invention relates to the reaction products of phenyl isocyanate and oligomers which are reaction products of an aliphatic polyhydroxyl compound, acrylamide or methacrylamide and formaldehyde. These reaction products, upon exposure to radiation, cure to form coatings and films.

BACKGROUND OF THE INVENTION

Oligomers, which are the reaction products of aliphatic polyhydroxyl compounds, acrylamide and formaldehyde, can be cured by exposure to radiation to produce films or coatings. Preferably, the polyhydric compounds contain from 2 to 15 carbon atoms and most preferably 6 to 15 carbon atoms. Compositions of this type and the general method of preparation can be found in U.S. Pat. No. 3,799,910, Shingai, et al. Typical of the aliphatic polyhydroxyl compounds which can be incorporated in these oligomers are alkandiols such as ethylene glycol having the structural formula:

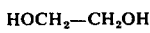

hydrogenated Bis Phenol A having the structural formula:

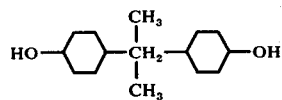

and alkantriols such as trimethylol propane having the structural formula:

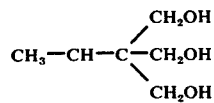

The major constituent of the reaction product mixture is an oligomer having the structural formula:

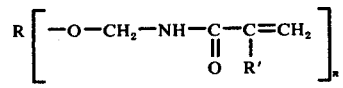

wherein $n$ is an integer of 1 or 2, $R'$ is hydrogen or a methyl group, when $n$ is 1, R is a monohydroxyalkyl group containing from 2 to 6 carbon atoms, a monohydroxycycloaliphatic group containing from 6 to 15 carbon atoms a dihydroxyalkyl group containing from 2 to 6 carbon atoms or a dihydroxycycloaliphatic group containing from 6 to 15 carbon atoms, when $n$ is 2, R is a monohydroxyalkyl group containing from 2 to 6 carbon atoms, or a monohydroxycycloaliphatic group containing from 6 to 15 carbon atoms.

The above oligomers are known compositions. It is also known the reaction product mixture containing these oligomers forms films and coatings upon exposure to radiation.

SUMMARY OF THE INVENTION

The phenyl isocyanate derivatives of the above oligomers are new compositions of matter having the structural formula:

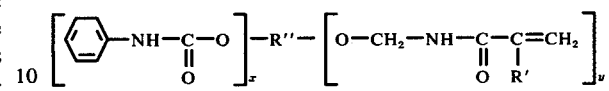

wherein $x$ is an integer of 1 or 2, $y$ is an integer of 1 or 2 and the sum of $x$ and $y$ may be 2 or 3, $R''$ is a saturated aliphatic hydrocarbon group containing from 2 to 6 carbon atoms or a cycloaliphatic group containing 6 to 15 carbon atoms and $R'$ is a hydrogen or methyl group. These new compositions of matter exhibit substantially higher surface electrical charge retention than the above oligomers. Coatings or films suitable for dielectric printing are obtained when about 20 to 100 equivalent percent based upon the hydroxyl value of the oligomer in the mixture resulting from the preparation of the oligomer is derivatized. The components of the mixture other than the oligomer contribute other properties such as stability to the final coatings or films. Optimum film or coating results are obtained when about 33 to 75 equivalent percent of the oligomer based upon the hydroxyl value of the oligomer in the reaction product mixture from the preparation of the oligomer is derivatized with phenyl isocyanate.

DETAILS OF THE INVENTION

The oligomers used as the starting materials for the new compositions of this invention are prepared by the reaction of (1) a polyhydroxyl aliphatic cyclic or straight chain compound such as a diol or triol, (2) acrylamide or methacrylamide and (3) formaldehyde. The polyhydroxyl component is usually employed in an amount of about 1 to 2 equivalents per equivalent of acrylamide and the formaldehyde is usually used in an amount of about 2 to 4 equivalents per equivalent of acrylamide. Excess formaldehyde can be present in the reaction mixture. The excess however does not enter into the reaction. A polymerization inhibitor such as hydroquinone is incorporated into the reaction mixture to prevent polymerization of the oligomer before radiation. The reaction can be conducted in a temperature range of about 105° to 150° C. and is preferably conducted in a temperature range of about 110° to 125° C. Usually a water immiscible solvent such as toluene, xylene or benzene is employed. Typical preparations of starting materials useful in the practice of this invention are shown below in Examples I and II.

When the polyhydroxyl component in the above reaction is a diol the structural formula of the resulting oligomer is:

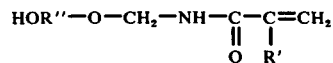

wherein $R''$ and $R'$ are described above.

When the polyhydroxyl component in the above reaction is a triol the structural formula of the resulting oligomer is:

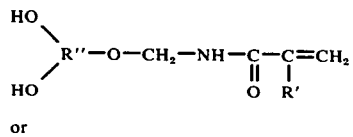

or

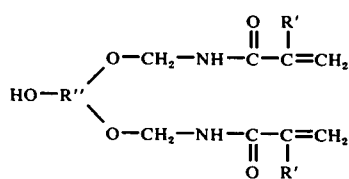

wherein R" and R' are described above.

To produce the new compositions of matter of the present invention the above described starting materials are reacted with phenyl isocyanate. The reaction can be conveniently conducted at ambient room temperature of about 23° C and 100° C. At a temperature of about 25° C. the reaction will go to completion in about 24 hours. At a temperature of about 100° C. the reaction will go to completion in about 1 hour. The reaction is preferably conducted at a temperature between about 85° and 95° C. Preferably, the reaction is conducted in the presence of a catalyst such as dibutyltin dilaurate.

The reaction product of the phenyl isocyanate and oligomer have the following structural formulae depending upon the hydroxyl number of polyhydric alcohol incorporated into the original oligomer as shown above:

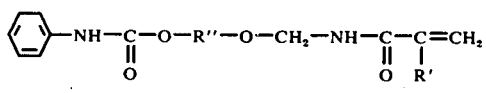 (1)

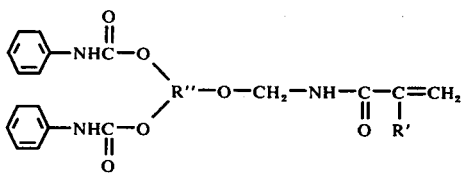 (2)

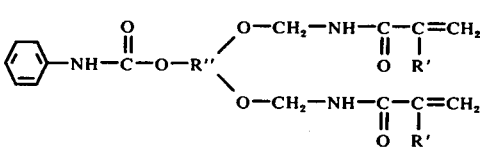 (3)

wherein R" and R' are described above.

The reaction product of the phenyl isocyanate and said oligomers like the original oligomers can be cured by exposure to ultraviolet light or an electron beam. When ultraviolet light is used a sensitizing agent such as butyl benzoin ether is preferably employed to promote curing. Sensitizers are not generally used when radiation is by means of an electron beam.

The above compositions are particularly useful in making films and coatings which include the underivatized oligomer. The underivatized oligomer used for films and coatings is usually formed in a reaction mixture which includes other materials to produce given film or coating properties. Commonly added to the reaction mixture are some monohydroxyl components such as hydroxyethyl acrylate and hydroxy Cardura E Acrylate. Hydroxy Cardura acrylate can be prepared by reacting Cardura E Ester sold by Shell Chemical Co. under that trade name with acrylic acid as shown in Example III. The exact structure of Cardura E Ester is unknown but it is the glycidyl ester of a mixture of aliphatic monocarboxylic acid containing 9 to 11 carbon atoms. The added components are incorporated into the reaction mixture to adjust the cure rate and hardness of the films or coatings. These components do react with part of the acrylamide and formaldehyde in the reaction mixture and in that respect compete with the aliphatic polyhydroxyl component of the original oligomer. Once reacted with acrylamide however they can not react further with phenyl isocyanate in the derivatization reaction. If an excess of hydroxyethyl acrylate or hydroxy Cardura acrylate is present, these excess molecules will react with phenyl isocyanate to form incidental urethanes.

Set out below are specific examples of typical preparations of the starting materials and the compositions of this invention. These examples are not intended to limit the scope of the invention.

Various tests are referred to in the following examples. Viscosity was measured by the Gardner method which can be found in ASTM D-1545-63. Color was measured by the Gardner method which can be found in AOCS Td 1A-64. The hydroxyl number was measured by the method set out in Analytical Chemistry, 1963, Vol. 35, pp. 571 to 573. Sward Rocker Hardness was measured according to ASTM D-2134–66.

EXAMPLE I

A. OLIGOMER PREPARATION

The following components were charged into a stirred heated kettle equipped with a sparge tube, condenser and water separator.

|  | Moles | Equivalent |
| --- | --- | --- |
| Hydrogenated Bis Phenol A | 0.38 | 0.76 |
| Hydroxyethyl Acrylate | 0.36 | 0.36 |
| Hydroxy Cardura Acrylate* | 0.35 | 0.35 |
| Acrylamide | 0.745 | 0.745 |
| Hydroquinone | .00322 | .00644 |
| Toluene 160.9 grams |  |  |
| Formalin (37%) | 1.48 | 2.96 |

*Obtained by reacting Cardura E Ester® sold by Shell Chemical Co. with acrylic acid (see Example IV)

A nitrogen sparge was used until the temperature reached 50° C. when it was switched to an air sparge. Heating was continued until the temperature reached 90° C. It was held at this temperature until a homogeneous solution was obtained which required about 40 minutes. The formaldehyde was then added, heating continued, and the water which azeotropes off was removed. Heating was continued until essentially all of the water came off. During the heating period which required 4 or 5 hours the pot temperature slowly rose to about 140° C. At the end the material in the pot was cooled to 90° C. and the toluene stripped off at this temperature under vacuum. The stripped material was filtered to give a clear product.

Viscosity = 11 stokes
Color = Gardner 1
Hydroxyl No. = 267

B. OLIGOMER REACTED WITH PHENYL ISOCYANATE

The above reaction product was mixed with phenyl isocyanate in the amounts shown in Table I and a small amount of dibutyltin dilaurate as catalyst. The mixture was left to stand at room temperature for a period of 18 hours. The reaction product was cured by passing a film of the material under a ⅜ inch slit from a 200 watt/inch high pressure mercury arc lamp at 60 feet per minute.

TABLE I

| Amount of Oligomer (equivalents) hydroxyl value | Amount of Phenyl (equivalents) | Amount of Dibutyltin Dilaurate | Rocker Hardness |
|---|---|---|---|
| .0475 | .0084 | 1 drop | 23 |
| 0.475 | .0168 | 1 drop | 19 |
| 0.475 | .025 | 1 drop | 23 |
| 0.475 | 0 | — | 7 |

EXAMPLE II

A. PREPARATION OF OLIGOMER

An oligomer was prepared from the following components using the procedure of Example I.

| | Equivalents |
|---|---|
| Trimethylol propane | .06 |
| Hydroxyethyl acrylate | .062 |
| Acrylamide | .062 |
| Toluene 568 grams | |
| Hydroquinone (9.48 grams) | |
| Formalin | .252 |

The product has the following properties:
- Viscosity = 3 stokes
- Color = gardner 1
- Hydroxyl No. = 265

B. OLIGOMER REACTED WITH PHENYL ISOCYANATE

The above reaction product was mixed with phenyl isocyanate and a dibutyltin dilaurate catalyst in the following amounts:

| | Equivalent |
|---|---|
| Oligomer | .0945 |
| Phenyl isocyanate | .0672 |
| Dibutyltin dilaurate 1 drop | — |

The above materials were mixed and left to stand for 1 day at room temperature.
Viscosity = 98.5 stokes

EXAMPLE III

ELECTRICAL CONDUCTIVITY MEASUREMENT

The oligomers prepared in Examples I, II and III and their phenyl isocyanate derivatives were individually tested for electrical conductivity using the following procedure.

The materials were mixed with styrene to reduce their viscosity to the range of from one to 10 stokes. The amount of styrene required was in the range of from 5% to 10% by weight of the total mixtures. Butyl benzoin, sold under the trade name Trigonal 14 by the Noury Chemical Corp., was added to the mixtures in an amount of 5% by weight of each individual mixture. The mixtures were coated on base paper stock sold under the trade designation of No. 2920 by Crown Zellerbach. The coatings were cured by passing them under a ⅜ inch slit of a high pressure Mercury Arc Lamp (Hanovia 200 watt/inch — Sun Graphic Systems — Quality Control Test Unit) at a rate of 70 feet per minute for four passes. The cured sheets were conditioned for a period of 16 hours at 50% relative humidity and a temperature of 72° F. before testing for electrical properties. To test the electrical properties, the coatings were charged for two seconds at 50 μ amps corona current and allowed to decay for 9 seconds. The retention of the charge by the individual coatings is shown below in Table II.

TABLE II

| Coating Material | Coating Weight | Charge Acceptance | Charge Retention | % Retention |
|---|---|---|---|---|
| Example 1 - Oligomer | 6.3 | 40 | 0 | 0 |
| Example 1 - Oligomer | 4.2 | 25 | 0 | 0 |
| Example 1-2 - Phenyl Isocyanate Derivative | 4.1 | 220 | 170 | 77 |
| Example 2 - Oligomer | 6.8 | 30 | 0 | 0 |
| Example 2 - Phenyl Isocyanate Derivative | 6.5 | 240 | 240 | 100 |
| Example 2 - Phenyl Isocyanate Derivative | 3.8 | 80 | 80 | 100 |

EXAMPLE IV

PREPARATION OF HYDROXY CARDURA ACRYLATE

The following reactants were charged into a 3 liter round bottom flask equipped with an air driven stirrer, a dropping funnel, and a thermo couple controller to read temperature and furnish heat through a mantle heater.

| | Equivalents | Grams | Moles |
|---|---|---|---|
| Cardura E ester® (Shell Chem. Co.) | | 980 | 4 |
| Acrylic Acid | | 328 | 4.56 |
| Dimethyl benzyl amine | | 5 | |
| Hydroquinone | | 2.8 | |

The flask was charged with cardura ester, heated to a temperature of 125°–130° C., flushed with nitrogen. Dimethyl benzyl amine and hydroquinone were added and the heat removed. The acrylic acid was then added by the dropping funnel over a period of 15 minutes. Cooling was required during the addition to keep the temperature between 125° and 133° C. When there was no appreciable exothermic reaction the reaction mixture was maintained at a temperature of 130° C. for an additional 2 hours. The product had an acid value of 22, a hydroxyl value of 210 and a Gardner viscosity of D.

The embodiments of the invention in which an exclusive property or privilege is claimed are defined as follows:

1. A composition of matter capable of curing upon exposure to radiation, said composition having the structural formula:

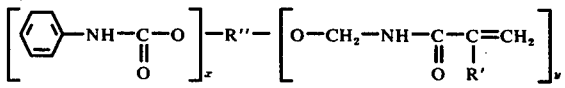

wherein $x$ is an integer of 1 to 2, $y$ is an integer of 1 to 2, and the sum of $x$ and $y$ is an integer 2 to 3, R″ is a saturated aliphatic hydrocarbon group containing from 2 to 6 carbon atoms or a cycloaliphatic group containing 6 to 15 carbon atoms and R′ is a hydrogen or methyl group.

* * * * *